| United States Patent [19] | [11] Patent Number: 4,885,417 |
|---|---|
| Kubiak | [45] Date of Patent: Dec. 5, 1989 |

[54] METHOD FOR THE DECOLORATION OF CHLORO-XYLENE COMPOSITIONS

[75] Inventor: Kenneth F. Kubiak, Cheektowaga, N.Y.

[73] Assignee: Occidental Chemical Corporation, Niagara Falls, N.Y.

[21] Appl. No.: 246,485

[22] Filed: Sep. 19, 1988

[51] Int. Cl.$^4$ .............................................. C07C 17/38
[52] U.S. Cl. .................................. 570/211; 570/207; 570/262; 570/264
[58] Field of Search ............... 570/198, 207, 211, 262, 570/264

[56] References Cited

U.S. PATENT DOCUMENTS

| 1,804,458 | 5/1931 | Brittin | 570/211 |
|---|---|---|---|
| 2,694,738 | 11/1954 | Rucker | 570/198 |
| 2,767,226 | 10/1956 | Weimer et al. | 570/211 |
| 3,691,239 | 9/1972 | Hackett | 570/262 |
| 3,850,998 | 11/1974 | Eilingsfeld et al. | 570/211 |

FOREIGN PATENT DOCUMENTS

| 1016621 | 10/1976 | Japan | 570/211 |
|---|---|---|---|
| 859110 | 1/1961 | United Kingdom | 570/211 |

*Primary Examiner*—Werren B. Lone
*Attorney, Agent, or Firm*—James F. Tao; Arthur S. Cookfair

[57] ABSTRACT

Off-color liquid ortho-chloro-para-xylene compositions are decolorized by contacting the compositions with particles of diatomaceous silica, magnesium oxide or soda ash.

6 Claims, No Drawings

METHOD FOR THE DECOLORATION OF CHLORO-XYLENE COMPOSITIONS

BACKGROUND OF THE INVENTION

1. Field of the Invention

This invention relates to a method for improving the color of chloro-xylene compositions.

Chloro-xylenes, such as ortho-chloro-para-xylene, are used for various commercial purposes, including the preparation of polymers for films and the like.

2. Description of the Prior Art

It is known in the art to purify liquid organic materials by contact with a suitable adsorbent. The advocacy of a particular purification process through the use of adsorbent materials will depend not only on the adsorbent selected, but on the nature of the liquid to be purified and the impurity to be removed.

U.S. Pat. No. 2,767,226 to Weimer et al discloses the purification of chlorinated benzenes, especially 1,2,4,5-tetrachlorobenzene by removal of dissolved metallic contaminants through the action of an adsorbing agent, such as, a clay, silica gel, calcium hydroxide, magnesium oxide, calcium oxide or calcium carbonate.

U.S. Pat. No. 1,804,458 to Britton discloses the purification of halogenated hydrocarbons such as benzyl chloride, or benzotrichloride by contact with water or a dilute solution of caustic soda, sodium carbonate, or other alkaline compound. After separation of the water the washed product is dried by treatment with a drying agent and/or absorbing agent such as calcium chloride or fillers.

U.S. Pat. No. 2,694,738 to Rucker teaches the treatment of chlorinated hydrocarbons, such as hexachlorocyclohexane, by filtration through an adsorbent, such as, fuller's earth, attapulgus clay, alumina, silica gel or activated carbon, to remove impurities.

Ortho-chloro-para-xylene, in relatively pure form is a substantially colorless liquid typically characterized by color specification of less than about 20 APHA. (APHA denotes a color unit system based on a visual comparison of a sample with standardized aqueous solution of potassium chloro-platinate and cobaltous chloride. The system is described in detail in Standard Methods For The Examination of Water and Waste Water, 15th Ed., American Public Health Association, New York, 1981, pps. 60-63.) Frequently, while in storage or shipment in drums, trailers, tank cars, and the like, ortho-chloro-para-xylenes will develop an undesirable color. The specific cause of discoloration is uncertain. However, since the off-color material is generally unacceptable, it is often necessary to return and re-distill such material. The additional transportation, handling, and re-distillation may add substantially to the overall cost of the chloro-xylene. It will be apparent that a need exists for a simple and inexpensive method to treat off-color material on-site, and thus eliminate the transportation and other costs associated with the return and re-distillation.

SUMMARY OF THE INVENTION

It has now been found that liquid chloro-para-xylene compositions may be decolorized by contacting the compositions with particles of diatomaceous silica, magnesium oxide, or soda ash and separating the solid materials. The preferred particulate material is magnesium oxide. The process may be carried out by adding the particulate material to a container of the chloro-para-xylenes, preferably with some agitation to increase contact of the liquid material with the particles, allowing the particles to settle and decanting the supernatant liquid. Preferably the ortho-chloro-para-xylene is passed through a filter bed of the particulate material, for example, by forming a mixture or slurry of the particles in the liquid and then filtering the mixture allowing the particulate material to form a filter bed through which the liquid is passed.

DETAILED DESCRIPTION OF THE INVENTION

In a preferred embodiment the process of this invention comprises passing a liquid ortho-chloro-para-xylene composition through a bed of magnesium oxide particles.

The following specific examples are provided to further illustrate this invention in the manner in which it may be practiced. It will be understood, however, that the specific details given in the examples have been chosen for purposes of illustration and are not to be construed as a limitation on the invention.

EXAMPLE 1

To a 76.7 gram sample of off-color ortho-chloro-para-xylene (APHA color =60) was added 81.3 grams of powdered magnesium oxide (reagent grade). The mixture was agitated by simple shaking and contents of the mixture were vacuum-filtered through a Buchner funnel with a recovery of 62.7 grams of decolorized chloro-para-xylene having an APHA color of 10.

EXAMPLE 2

The procedure of Example 1 was repeated except that 75.2 gram of o-chloro-p-xylene and 18.0 grams of anhydrous sodium carbonate was employed (in place of magnesium oxide). There was obtained 70.0 grams of chloro-para-xylene having an APHA color of 20.

EXAMPLE 3

For purposes of comparison, 75 grams of o-chloro-p-xylene having a APHA color of 60, was vacuum-filtered through a Buchner funnel with a Whatmann No. 50 filter paper. There was recovered 74.0 grams of chloro-para-xylene with an APHA color of 40-50.

EXAMPLE 4

75.0 grams of o-chloro-p-xylene (APHA color=60) was vacuumfiltered through a Buchner funnel packed with a diatomaceous silica (Dicalite Speedplus, GREFCO, Inc., Los Angeles, Calif.) and a Whatmann No. 4 filter paper. There was recovered 49.5 grams of chloro-para-xylene with an APHA color of 5 to 10.

EXAMPLE 5

74.9 grams of o-chloro-p-xylene (APHA color=60) was vacuumfiltered through a Buchner funnel packed with magnesium oxide (Baker analyzed reagent) and Whatmann No. 4 filter paper. There was recovered 55.1 grams of chloro-para-xylene with an APHA color of 5 to 10.

EXAMPLE 6

2.2 grams of diatomaceous silica (dicalite Speedplus, Grefco, Inc., Los Angeles, Calif.) was combined with 64.0 grams of o-chloro-p-xylene (APHA color of 60) in a laboratory flask. The contents were intimately mixed by shaking the flask and then allowed to settle over a period of about 60 hours. The clear upper layer of clear liquid, after removal by decant was found to have an APHA color of 10.

What is claimed is:

1. A process for removing discoloration from an off-color liquid ortho-chloro-para-xylene composition which comprises contacting the liquid ortho-chloro-para-xylene composition with particulate material selected from the group consisting of magnesium oxide, diatomaceous silica, or soda ash, separating the particulate material and recovering decolorized ortho-chloro-para-xylene.

2. The process of claim 1 wherein the particulate material is magnesium oxide.

3. The process of claim 1 wherein the particulate material is diatomaceous silica.

4. The process of claim 1 wherein the particulate material is soda ash.

5. A process according to claim 1 wherein the particulate material is mixed with the off-color liquid ortho-chloro-para-xylene and the mixture is filtered to separate the particulate material and recover the decolorized ortho-chloro-para-xylene.

6. A process according to claim 1 wherein the particulate material is separated by allowing the particles to settle and decanting the decolorized ortho-chloro-para-xylene.

* * * * *